United States Patent [19]

Bachmann et al.

[11] Patent Number: 4,479,803
[45] Date of Patent: Oct. 30, 1984

[54] AGENT FOR OXIDATIVE DYEING OF HAIR

[75] Inventors: Heinrich Bachmann, Giffers; Plato Portmann, Fribourg, both of Switzerland

[73] Assignee: Wella Aktiengesellschaft, Darmstadt, Fed. Rep. of Germany

[21] Appl. No.: 253,510

[22] PCT Filed: Sep. 25, 1980

[86] PCT No.: PCT/EP80/00103
§ 371 Date: Apr. 8, 1981
§ 102(e) Date: Apr. 8, 1981

[87] PCT Pub. No.: WO81/00810
PCT Pub. Date: Apr. 2, 1981

[30] Foreign Application Priority Data

Sep. 28, 1979 [DE] Fed. Rep. of Germany ....... 2939303

[51] Int. Cl.$^3$ ................................................ A61K 7/13
[52] U.S. Cl. ........................................... 8/406; 8/407; 8/408; 8/424
[58] Field of Search ................... 8/424, 406, 407, 408

[56] References Cited

U.S. PATENT DOCUMENTS

| | | | |
|---|---|---|---|
| 2,944,869 | 7/1960 | Kalopissis et al. | 8/424 |
| 3,957,424 | 5/1976 | Zeffren et al. | 8/424 |
| 4,170,452 | 10/1979 | Grollier et al. | 8/424 |
| 4,212,645 | 7/1980 | Leon et al. | 8/406 |
| 4,289,495 | 9/1981 | Bugaut et al. | 8/406 |

FOREIGN PATENT DOCUMENTS

| 8100810 | 2/1981 | European Pat. Off. | 8/424 |
|---|---|---|---|
| 2013728 | 8/1979 | United Kingdom . | |

OTHER PUBLICATIONS

Chemical Abstracts 91: 154555a, (1979).
Chemical Abstracts 94: 47291b, (1980).

Primary Examiner—Albert T. Meyers
Assistant Examiner—John M. Kilcoyne
Attorney, Agent, or Firm—Michael J. Striker

[57] ABSTRACT

Use is made in the oxidative dyeing of hair of a preliminary coloring stage of the general formula

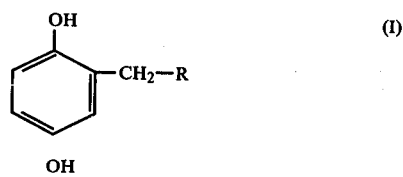

wherein R signifies COOR', CONH$_2$, CONHR', CONR'$_2$, CONH—NH$_2$, CONH—OH, CN, CH$_2$OH, CHO, CH(OH)(OR'), CH(OR')$_2$ and R' represents an alkyl group with 1 to 5 carbon atoms. The preliminary coloring stages as per formula (I) may be contained in the hair dyeing agents singly or in a mixture with known preliminary coloring stages and/or direct-acting hair dyeing agents. The hair dyeing agents may, in particular, additionally contain amino acids present in nature, their esters and/or their amides. The hair dyeing agents as described, are well compatible physiologically and it will particularly be brown to reddish-brown colorings having a natural effect, that may be obtained by their use.

5 Claims, No Drawings

AGENT FOR OXIDATIVE DYEING OF HAIR

For the dyeing of hair, it is the so-called oxidative colorants that have obtained essential importance by reason of their being fast to light and washing. To produce the oxidative colorants, certain aromatic compounds capable of oxidative coupling are being applied onto the hair as preliminary coloring stages. These will partially penetrate the hair and be oxidized therein to the desired colorant, either by atmospheric oxygen or, particularly, by the addition of chemical oxidants such as hydrogen peroxide.

Mainly the derivatives of diamino or hydroxyamino compounds of benzene, naphthalene, pyridine, pyrimidine, pyrazolone, indol and chinoline serve as preliminary coloring stages. In part due to physiological reasons, the aforenoted materials are not entirely unobjectionable.

Deriviatives of diphenol and naphthol are also known as preliminary coloring stages. However, no intensive hair dyeing has been achieved so far with representatives of these classes of substances known hitherto as preliminary coloring stages.

Also, as knowledge concerning the formation of hair pigment has been obtained, the use of tyrosine,Dopa+), and Dihydroxyindols for the dyeing of hair has been described. Preparations on the basis of these compounds, which are physiologically the most suitable for use as preliminary coloring stages, could not, however, for various reasons, gain acceptance in practice.

+) Dopa=L-$\beta$-(3,4-dihydroxy-phenyl)-alanine

Numerous particular demands are put forward with respect to oxidative colorants used for dyeing human hair. They must be unobjectionable as to toxicology and dermatology, and allow for colorings of the desired intensity. It is furthermore necessary that a wide spectrum of various coloring nuances be obtained by a combination of such compounds as are suitable for preliminary coloring stages. In addition, the hair colorings that can be obtained are required to demonstrate good fastness to light and resistance to permanent-wave treatment, acids and rubbing. Such colorings must, at any rate, remain stable against the influence of light, rubbing and chemical agents, for a period of at least four to six weeks.

The plurality of the demands as put forward are not met to complete satisfaction by the compounds used at present as preliminary coloring stages in oxidative hair dyeing agents.

The task existed therefore, to prepare agents for oxidative dyeing of hair, based upon such compounds serving as preliminary coloring stages which, physiologically have more suitable properties when compared to known compounds used as preliminary coloring stages. These compounds should, furthermore, possess good fastness to wearing and a sufficient intensity of the colorings, either alone, or in combination with other compounds known as preliminary coloring stages.

The object of the invention is, therefore, an agent for oxidative dyeing of hair, characterized by containing as preliminary coloring stage, a minimum of one compound of the general formula

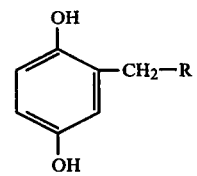

(I)

wherein R signifies COOR', CONH$_2$, CONHR', CONR'$_2$, CONH—NH$_2$, CONH—OH, CN, CH$_2$OH, CHO, CH(OH)(OR'), CH(OR')$_2$ and R' represents an alkyl group with 1 to 5 carbon atoms.

The total content of these compounds according to formula (I), serving as preliminary coloring stage, should amount to approximately 0.1 to 6 percent by weight, preferably 1 to 4 percent by weight.

Examples of suitable compounds, contained as preliminary coloring stages in the hair dyeing agents of the aforenamed general formula (I) are, in particular Homogentistic acid amide,
Homogentisic acid dimethylamide,
Homogentisic acid methylester,
Homogentisic acid ethylester,
Homogentisic acid isopropylester and
Homogentisic hydroxamic acid (2,5-Dioxyphenyl acetohydroxamic acid).

Furthermore, the agents for dyeing hair of the present application may, in particular, contain as preliminary coloring stages, such aromatic compounds as occur in nature, but also other aromatic compounds having a minimum of one hydroxy group in the molecule, and which may additionally have a nitrogen atom or a plurality of nitrogen atoms in the molecule.

Examples of such compounds are:

(a) aromatic compounds containing in the molecules a minimum of one hydroxy group such as orcin, hydroquinone, pyrogallol, hydroxy-hydroquinone, protecatechualdehyde, thymol, guajacol, arbutin, pyrocatechol, juglone, lawsone, vanillin, pulvinic acid, hydroxycoumarin, flavonoids, and grevillines, derivatives of salicylic acid, caffeic acid, chlorogenic acid, as well as, (b) aromatic compounds with at least one hydroxy group and additionally a minimum of one nitrogen atom in the molecule, such as Dopa, tyrosine, kynurenic acid and xanthurenic acid, derivatives of anthranilic acid, nicotinic acid, isonicotinic acid, picolinic acid, pyrrols, pyrimidines, purines, betalainic acids, kynurenin, and ommatins.

These compounds may be used in a ratio of 0.1 to 1 mol, relative to 1 mol of the compounds of the general formula (I) contained as preliminary coloring stages in the agents described herein.

The total quantity of compounds serving as preliminary coloring stages in the hair dyeing agents according to the invention will suitably amount to approximately 0.1 to 6 percent by weight, preferably 1 to 4 percent by weight.

It is, furthermore, possible for the hair dyeing agents to additionally contain usual direct-acting hair colorants.

To increase the coloring depth of the hair colorings, the dyeing agents according to the the present application may, furthermore, contain amino acids occurring in nature, their esters with lower alcohols and/or their amides as well as mono or dialkyl amides, wherein the alkyl group bonded to the nitrogen of the amide, will have 1 to 5 carbon atoms. Examples thereof are the amino acids: glycine, alanine, proline, hydroxy proline, serine, cysteine, histidine and tryptophane, their esters with lower alcohols as well as their respective amides or mono or dialkyl amides, wherein the alkyl group bonded to the nitrogen of the amide will have 1 to 5 carbon atoms. The amino acids and their aforenamed derivatives may be contained in the agents particularly in a proportion of 0.05 to 1 mol relative to 1 mol of the compounds present therein as preliminary coloring stages.

Finally, there may additionally be present in the hair dyeing agents usual cosmetic additives, for instance antioxidants such as ascorbic acid or sodium sulfite, alkalizing agents such as alkaline hydroxides, ammonium or, respectively, alkaline carbonate and ammonium, or, respectively, alkaline hydrogen carbonate, organic acids such as, for instance, acetic acid, lactic acid and citric acid, solvents, perfumes, swelling agents, wetting agents, emulgators, thickeners, hair-care substances and others.

The preparation may be made available as a solution, preferably, however, as a cream, a gel or an emulsion. Its composition represents a mixture of the colorants with usual constituents of such preparations. The usual constituents of creams, gels or emulsions coming into consideration will, for instance, be wetting agents or emulgators from the categories of anionic, cationic or non-ionogenic surfactants such as sulfates of fatty alcohols, alkyl sulfonates, alkylbenzene sulfonates, salts of alkyl trimethyl ammonia, oxethylated fatty alcohols, oxethylated nonylphenols, fatty acid alkanol amides and, furthermore, thickeners such as higher fatty alcohols, starch, cellulose derivatives, paraffin oil and fatty acids, as well as hair-care substances such as lanolin derivatives, cholesterol and pantothenic acid. The constituents as noted are used in quantities as usual for these purposes, i.e. wetting agents and emulgators in concentrations of approximately 0.5 to 30 percent by weight, while thickeners may be present in the preparations in a quantity of approximately 0.1 to 25 percent by weight.

Depending upon their composition, the dyeing agents according to the invention may react weakly acidic, neutral or alkaline. They are, in particular, of a pH value in the alkaline range of 7.5 to 11, adjustment being preferably made with ammonia, or ammonium hydrogen carbonate. Use may also be made of organic amines such as mono or triethanolamine.

Application may be made, depending upon the pH value of these agents as per invention, (A) in one, (B) in two, or (C) in three stages.

(A) In the one-stage process, the hair dyeing agent is mixed with an oxidant shortly before use, and the mixture applied onto the hair. Coming into consideration as oxidants for developing the hair coloring are, mainly, peroxodisulfates or hydrogen peroxide, the latter, for instance, as 3% aqueous solution, or, respectively, additive compounds of the latter with urea, melamin or sodium borate. The application temperatures of these hair dyeing agents are in the range from 20° to 50° C. After an application period of approximately 20 to 40 minutes, preferably 30 minutes, the hair is rinsed with the aqueous solution of a weakly organic acid, for instance a solution of citric acid or tartaric acid which, in given instances, may additionally contain EDTA[+], and final rinsing is made with water.

[+] EDTA=Ethylenediaminetetraacetate

This process is particularly suitable for the application of such hair dyeing agents according to the invention that are set to a pH value of approximately 9 to 10.

(B) The two-stage process is suitable for the application of the hair dyeing agents described herein, particularly when these are of a pH value between 7 and 8. The hair dyeing agent is therein applied onto the hair in the first stage, and allowed to act at a temperature of 20° to 50° C. for approximately 10 to 20 minutes. In the following second stage, a 1 to 8% alkaline solution of a suitable oxidant is applied onto the hair, whereby the pH value of the mixture acting upon the hair will rise to approximately 9.5. This solution is also allowed to act for approximately 10 to 20 minutes. Subsequently, the hair is rinsed with the aqueous solution of a weak organic acid, as for instance citric acid or tartaric acid containing in given instances also EDTA, and final rinsing is made with water.

(C) The three-stage process is suitable for such hair dyeing agents as per invention which have a pH value within the weakly acidic range. Herein, the hair dyeing agent is applied onto the hair in the first stage and allowed to act for approximately 10 minutes at a temperature of approximately 35° to 45° C. In the second process stage, an oxidant, for instance a 10% suspension of ammonium peroxodisulfate is brought onto the hair and also allowed to act for about 10 minutes at the same temperature. Finally, in the third process stage, the aqueous solution of an alkalizing agent is distributed onto the hair and allowed to act for approximately 15 minutes at the same temperature. Subsequently, the hair is first rinsed with an aqueous solution of a weak organic acid, such as of citric acid or tartaric acid containing, in given instances, also EDTA, and final rinsing is made thereupon with water.

The following embodiments shall explain the object of the invention in more detail.

EMBODIMENTS

EMBODIMENT 1

| | |
|---|---|
| 3.00 g | Homogentisic acid amide |
| 0.80 g | Orcin |
| 0.03 g | Glycine copper |
| 7.50 g | Guanidine hydrochloride |
| 2.00 g | Ammonium hydrogencarbonate |
| 1.00 g | Hydroxyethylcellulose, medium viscosity |
| 20.00 g | Ethanol |
| 65.67 g | Water |
| 100.00 g | |

This hair dyeing solution, having a pH value of 7.8, is applied onto bleached human hair and allowed to act thereon for 15 minutes at a temperature of 37° to 40° C. Subsequently, 50 mL of an aqueous solution of 5 percent by weight ammonia, and 1.5 percent by weight hydrogen peroxide, are applied onto the hair. This solution is also allowed to act for 15 minutes at the same temperature. The hair is then first rinsed with a 10% solution of citric acid containing also 0.05 percent by weight EDTA, and final rinsing is made with water. The hair has obtained a brown coloring of a natural effect.

EMBODIMENT 2

| | |
|---|---|
| 3.00 g | Homogentisic acid methylester |
| 0.80 g | Guajacol |
| 0.03 g | Glycine copper |
| 7.50 g | Guanidine hydrochloride |
| 2.00 g | Ammonium hydrogencarbonate |
| 1.00 g | Hydroxyethylcellulose, medium viscosity |
| 20.00 g | Ethanol |
| 65.67 g | Water |
| 100.00 g | |

Application of this hair dyeing solution, having a pH value of 7.8 is made as described in embodiment 1. Dark brown, natural human hair will, after treatment, have obtained a natural-looking neutral brown coloring.

EMBODIMENT 3

| | |
|---|---|
| 3.00 g | Homogentisic acid ethylester |
| 1.00 g | Orcin |
| 0.50 g | Glycine methylester |
| 0.03 g | Glycine copper |
| 7.50 g | Guanidine hydrochloride |
| 2.00 g | Ammonium hydrogencarbonate |
| 1.00 g | Hydroxyethylcellulose, medium viscosity |
| 20.00 g | Ethanol |
| 64.97 g | Water |
| 100.00 g | |

This hair dyeing solution, having a pH value of 7.8, is applied onto grey human hair that has not been pretreated, and allowed to act for 15 minutes at a temperature from 37° to 40° C. Subsequently, 50 mL of an aqueous solution of 5% by weight ammonia and 1.5% by weight hydrogen peroxide are applied onto the hair. This solution is also allowed to act for 15 minutes at the same temperature. The hair is then rinsed, first with a 10% solution of citric acid additionally containing 0.05% by weight EDTA, and finally with water. The hair has obtained a reddish-brown coloring.

EMBODIMENT 4

| | |
|---|---|
| 2.00 g | Homogentisic acid isopropylester |
| 1.00 g | Homogentisic hydroxamic acid |
| 0.50 g | Guanidine |
| 0.50 g | Proline methylester |
| 0.03 g | Glycine copper |
| 7.50 g | Guanidine hydrochloride |
| 2.00 g | Ammonium hydrogencarbonate |
| 1.00 g | Hydroxyethylcellulose, medium viscosity |
| 20.00 g | Ethanol |
| 65.47 g | Water |
| 100.00 g | |

This hair dyeing solution, having a pH value of 7.8, is applied onto bleached human hair and allowed to act for 15 minutes at a temperature of 37° to 40° C. Subsequently, 50 mL of an aqueous solution of 5% by weight ammonia and 1.5% by weight hydrogen peroxide, are applied onto the hair. This solution is also allowed to act for 15 minutes at the same temperature. Subsequently, the hair has obtained a reddish-hued dark brown coloring.

EMBODIMENT 5

| | |
|---|---|
| 3.00 g | Homogentisic acid dimethylamide |
| 1.00 g | Guajacol |
| 0.50 g | Glycine amide |
| 0.03 g | Glycine copper |
| 9.50 g | Guanidine hydrochloride |
| 1.00 g | Ammonium hydrogencarbonate |
| 2.50 g | Ammonia |
| 0.35 g | Sodium hydrogensulfite |
| 1.00 g | Hydroxyethylcellulose, medium viscosity |
| 40.00 g | Ethanol |
| 41.12 g | Water |
| 100.00 g | |

This hair dyeing solution is mixed shortly before use with 20 mL hydrogen peroxide solution (3%), the mixture applied onto bleached human hair and allowed to act for 30 minutes at 37° to 40° C. The hair is subsequently rinsed, first with a 10% solution of citric acid additionally containing 0.05% EDTA, and finally with water. The hair has obtained a natural brown coloring without any reddish hue.

EMBODIMENT 6

| | |
|---|---|
| 2.00 g | Homogentisic acid isopropylester |
| 1.00 g | Homogentisic acid dimethylamide |
| 1.00 g | Glycine amide |
| 0.50 g | Proline methylester |
| 0.03 g | Glycine copper |
| 9.50 g | Guanidine hydrochloride |
| 1.00 g | Hydroxyethylcellulose, medium viscosity |
| 1.00 g | Citric acid |
| 30.00 g | Ethanol |
| 53.97 g | Water |
| 100.00 g | |

This hair dyeing agent in gel form is applied onto bleached human hair and allowed to act for 10 minutes at a temperature of 37° to 40° C. Subsequently, 25 mL of a 10% aqueous suspension of ammonium peroxodisulfate are evenly distributed over the hair and allowed to act for a further 10 minutes at the same temperature. The hair is subsequently rinsed, first with a 10% solution of citric acid additionally containing 0.05% by weight EDTA and finally with water. The hair has obtained a brown coloring.

All percentages quoted in the present application represent percent by weight.

We claim:

1. Aqueous composition for the oxidative dyeing of human hair, containing 0.1 to 6.0 percent by weight of a compound of the formula (I)

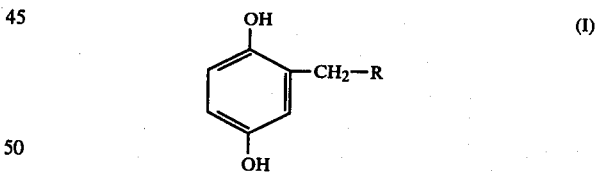

wherein R signifies COOR', CONH$_2$, CONHR', CONR'$_2$ or CONH—OH, with R' being an alkyl group with 1 to 5 carbon atoms.

2. Composition according to claim 1, wherein said compound of formula (I) is homogentisic acid amide, homogentisic acid dimethylamide, homogentisic acid methylester, homogentisic acid isopropylester or homogentisic hydroxamic acid.

3. Composition according to claim 1, having a pH ranging from 7.5 to 11.

4. Composition according to claim 1, further containing 0.05 to 1 mol relative to 1 mol of the compound of formula (I) of an amino acid selected from the group consisting of glycine, alanine, proline, hydroxy proline, serine, cysteine, histadine, and tryptophane.

5. Composition according to claim 4, wherein said amino acid is provided in the form of glycine copper.

* * * * *